United States Patent
Uda

(10) Patent No.: US 7,352,845 B2
(45) Date of Patent: Apr. 1, 2008

(54) ENERGY DISPERSION TYPE X-RAY DIFFRACTION/SPECTRAL DEVICE

(75) Inventor: Masayuki Uda, Tokyo (JP)

(73) Assignee: Waseda University, Tokyo (JP)

( * ) Notice: Subject to any disclaimer, the term of this patent is extended or adjusted under 35 U.S.C. 154(b) by 0 days.

(21) Appl. No.: 10/563,238

(22) PCT Filed: Jul. 5, 2004

(86) PCT No.: PCT/JP2004/009535

§ 371 (c)(1), (2), (4) Date: Jan. 3, 2006

(87) PCT Pub. No.: WO2005/005969

PCT Pub. Date: Jan. 20, 2005

(65) Prior Publication Data

US 2006/0165218 A1    Jul. 27, 2006

(30) Foreign Application Priority Data

Jul. 11, 2003    (JP)    ............... 2003-196155

(51) Int. Cl.
*G01N 23/207* (2006.01)
*G01N 23/20* (2006.01)
*G01T 1/36* (2006.01)

(52) U.S. Cl. ............................. 378/73; 378/71; 378/70; 378/82

(58) Field of Classification Search ............ 378/44–50, 378/82–90, 70–80, 98.9, 210, 98.11–98.12
See application file for complete search history.

(56) References Cited

U.S. PATENT DOCUMENTS 3,440,419 A * 4/1969 Das Gupta et al. ........... 378/46
3,903,414 A * 9/1975 Herbstein et al. ............. 378/46
3,920,984 A * 11/1975 Kirkendall et al. ........... 378/49

(Continued)

FOREIGN PATENT DOCUMENTS

JP    59-97044    6/1984

(Continued)

OTHER PUBLICATIONS

Yellipeddi et al., Applications and Perspectives of a New Innovative XRF-XRD Spectrometer in Industrial Process Control, 2000, International Centre for Diffraction Data, Advances in X-ray Analysis, vol. 42, pp. 126-136.*

(Continued)

*Primary Examiner*—Edward J. Glick
*Assistant Examiner*—Anastasia S. Midkiff
(74) *Attorney, Agent, or Firm*—Westerman, Hattori, Daniels & Adrian, LLP.

(57) ABSTRACT

A white X-ray generating means and an X-ray detecting means are respectively moved to a first position and a second position that are separated, X-ray intensities, for each energy, detected at respective positions by the X-ray detecting means are obtained as first data and second data, a third data, that is refraction-X-ray-only data, is obtained based on the difference between the first data and the second data, and data about fluorescent X-ray is obtained from the difference between the first or second data and the third data.

3 Claims, 3 Drawing Sheets

U.S. PATENT DOCUMENTS

| | | | |
|---|---|---|---|
| 4,263,510 A * | 4/1981 | Ciccarelli et al. | 378/46 |
| 4,358,854 A * | 11/1982 | Marten et al. | 378/45 |
| 4,916,720 A * | 4/1990 | Yamamoto et al. | 378/81 |
| 5,369,275 A * | 11/1994 | Usui et al. | 250/310 |
| 5,406,608 A * | 4/1995 | Yellepeddi et al. | 378/46 |
| 5,491,738 A * | 2/1996 | Blake et al. | 378/71 |
| 5,745,543 A * | 4/1998 | De Bokx et al. | 378/45 |
| 6,285,734 B1 * | 9/2001 | von Alfthan | 378/46 |
| 6,285,736 B1 * | 9/2001 | Dosho | 378/79 |
| 6,751,287 B1 * | 6/2004 | Kalyon et al. | 378/71 |
| 6,885,727 B2 * | 4/2005 | Tamura | 378/45 |
| 2002/0057759 A1 * | 5/2002 | Ferrandino et al. | 378/84 |
| 2004/0109534 A1 * | 6/2004 | Uehara et al. | 378/84 |
| 2005/0069085 A1 * | 3/2005 | Lewis | 378/84 |

FOREIGN PATENT DOCUMENTS

| | | |
|---|---|---|
| JP | 7-35708 | 2/1995 |
| JP | 2000-283933 | 10/2000 |

OTHER PUBLICATIONS

Rindby et al., Micro-Distribution of Heavy Elements in Highly Inhomogeneous Particles Generated from u-beam XRF/XRD Analysis, 1997, Nuclear Instruments and Methods in Physics Research B, Elsevier, vol. 124, pp. 591-604.*

Cornaby et al., An XRD/XRF Instrument for the Microanalysis of Rocks and Minerals, 2001, IOP Publishing, Measurement Science and Technology, vol. 12, pp. 676-683.*

* cited by examiner

ENERGY DISPERSION TYPE X-RAY DIFFRACTION/SPECTRAL DEVICE

TECHNICAL FIELD

The present invention relates to an energy dispersion type X-ray diffraction/spectral device which detects diffracted rays and fluorescent X-rays simultaneously using white X-rays and with an X-ray detector fixed.

BACKGROUND ART

An X-ray diffraction device is known as a device which analyzes a crystalline structure of a specimen using X-rays. The X-ray diffraction device is constructed of an X-ray generating means disposed at a position from which it can irradiate the surface of a specimen at an angle $\theta$ and an X-ray detecting means such as a counter disposed at a position of angle $2\theta$ formed by the irradiation direction and measuring point of the specimen, and irradiates the specimen with X-rays having a known single wavelength $\lambda$ by sequentially rotating and moving the X-ray generating means and X-ray detecting means and measures intensity of X-rays at the angle $\theta$, that is, diffraction intensity.

Since diffracted X-rays are diffracted at the angle $\theta$ which satisfies:

$$2d \sin \theta = \lambda \quad \text{[Formula 1]}$$

according to Bragg's law, it is possible to know a crystal face spacing d and diffraction intensity of the specimen from the diffraction graphic and obtain data for determining an atomic arrangement of the specimen.

However, the X-ray diffraction device requires a precise mechanism for sequentially rotating and moving the specimen and X-ray detecting means, that is, a goniometer, which not only complicates the device and increases the size of the device but also requires a rotation/movement operation time and measuring time at each position of movement, producing a problem that it takes quite a long time to obtain a measurement result.

To solve such a problem, an energy dispersion diffraction method as described in Non-Patent Document 1 is proposed.

According to this method, an X-ray generation device is disposed at a position of an angle $\theta$ with respect to the surface of a specimen, a means for detecting energy and intensity of X-rays simultaneously is disposed at a position of an angle $2\theta$ formed by the irradiation direction and measuring point of the specimen, white X-rays are irradiated with $\theta$ and $2\theta$ fixed and intensity of X-rays having energy E is measured.

Bragg's law is expressed centered on energy E as:

$$E = h\nu = hc/\lambda = hc/2d \sin \theta \quad \text{[Formula 2]}$$

Therefore, it is possible to determine an atomic surface spacing d and diffraction intensity by only measuring the relationship between the detected energy E and intensity of diffracted X-rays by keeping the angles of the X-ray generating means, specimen and X-ray detecting means to fixed positions and using a multichannel analyzer or the like.

Furthermore, since the X-rays which reach the detecting means also include fluorescent X-rays from the specimen, if these X-rays can be distinguished from diffracted X-rays, it is also possible to determine the kind of atoms of the specimen from fluorescent X-rays.

The energy at which diffracted rays emerge follows Bragg's law and also depends on the angle $\theta$, and therefore there is also a proposal to conduct measurement at an appropriate angle at which diffracted rays and fluorescent X-rays do not overlap each other so as to distinguish diffracted rays from fluorescent X-rays.

Non-Patent Document 1: B. D. Cullity. Elements of X-Ray Diffraction, 2nd ed (Reading, Mass.: Addison-Wesley, 1977.)

DISCLOSURE OF THE INVENTION

Problems to be Solved by the Invention

However, when an area of emergence of fluorescent X-rays is limited, it is possible to separate diffracted rays from fluorescent X-rays, whereas such separation is not possible when there are many areas where fluorescent X-rays are generated, and moreover, it is necessary to precisely change $2\theta$ in order to search for an appropriate angle which varies from one specimen to another, which still produces a problem of complicating the structure of the measuring device.

Means for Solving the Problems

The present invention has been implemented in view of the above described problems and it is an object of this invention to provide an energy dispersion type X-ray diffraction/spectral device capable of removing interference between fluorescent X-rays and diffracted rays and accurately detecting only diffracted rays without complicating the structure of an X-ray detecting means.

In order to solve these problems, the present invention moves a white X-ray generating means and an X-ray detecting means to a first position and a second position respectively which are separate from each other, uses intensities of X-rays detected for each level of energy by the X-ray detecting means at the respective positions as first data and second data, obtains third data regarding diffracted X-rays from the difference between the first data and the second data and obtains data regarding fluorescent X-rays from the difference between the first or second data and third data.

EFFECTS OF THE INVENTION

As described above, the present invention only moves the white X-ray generating means and X-ray detecting means to two separated points, and can thereby simplify the structure, eliminate the time required for continuous rotation and measurement times at various angles and obtain both diffraction data and fluorescent X-ray data in a short time.

Furthermore, since no specimen rotation mechanism is required, it is possible to extremely simplify the structure and construct the device as a small and portable device.

BEST MODE FOR CARRYING OUT THE INVENTION

With reference now to the attached drawings, details of the present invention will be explained below.

Figure 1:
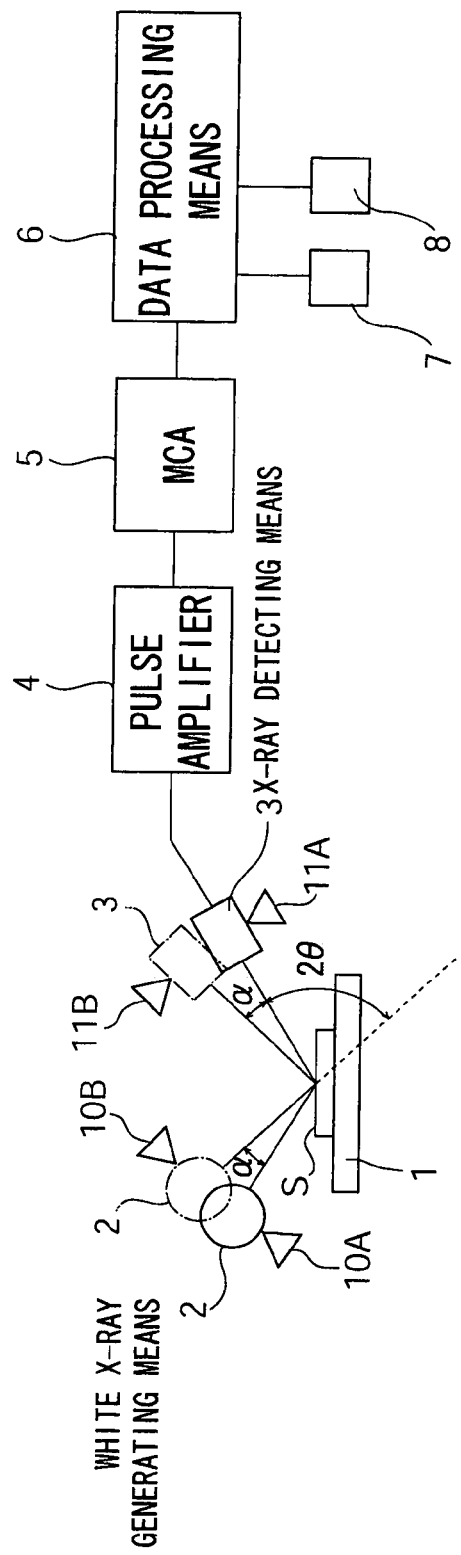
FIG. 1 is a block diagram showing an embodiment of an energy dispersion type X-ray diffraction/spectral device according to the present invention.

FIG. 1 shows an embodiment of an energy dispersion type X-ray diffraction/spectral device according to the present invention, in which a specimen support is interposed between a white X-ray generating means 2 and an X-ray detecting means 3, and a multichannel analyzer (MCA) 5 is connected to the output end of the X-ray detecting means 3 via a pulse amplifier 4.

The specimen support 1 is provided with positioning members 10A, 10B, 11A and 11B which move between a first position and a second position located a few degrees apart therefrom so as to shift only diffracted X-rays, that is, to relatively move the position by an angle α, this degree enough to prevent a variation in intensity of fluorescent X-rays as much as possible, and constructed so as to be fixed to a predetermined position by a notch mechanism or the like. Thus, the notch mechanism causes movement by a certain angle between the two points with high accuracy, and can thereby simplify the structure.

A data processing means 6 is provided with a first storing means 7 for storing intensity data for each level of energy of white X-rays irradiated onto the specimen and absorptivity data which takes into consideration absorption due to the air or the like which exists in the transmission path of X-rays and proportions of various elements constituting the specimen, and a second storing means 8 for storing data measured at the first position and second position.

In this embodiment, when the specimen S is placed on the specimen support 1, the white X-ray generating means 2 and X-ray detecting means 3 are set to the first position (position shown by a solid line in the figure) and a measurement is started, the X-ray detecting means 3 detects diffracted X-rays and fluorescent X-rays corresponding to elements constituting the specimen S and the crystalline structure thereof.

The data processing means 6 corrects X-ray intensity for each level of energy detected by the X-ray detecting means 3 based on the data of the first storing means 7 and stores the corrected X-ray intensity in the second storing means 8.

Next, the white X-ray generating means 2 and X-ray detecting means 3 are moved to the second position (position shown by dotted line in the figure), X-ray intensity for each level of energy detected by the X-ray detecting means 3 is corrected based on the data of the first storing means 7, data equivalent to that obtained by irradiating the specimen with X-rays of the same intensity over the entire energy area of X-rays is obtained and stored in the second storing means 8.

Figure 2:
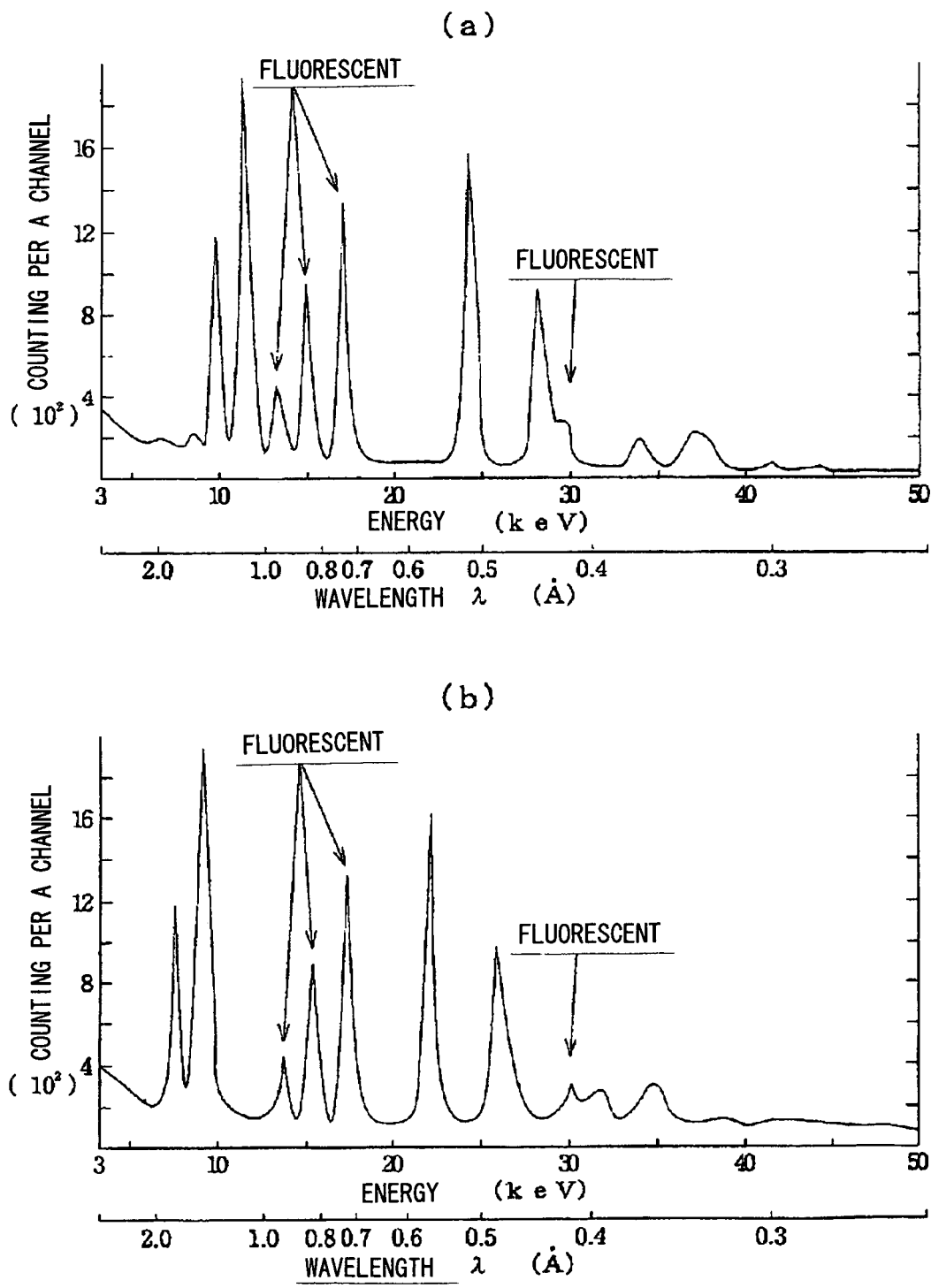
FIG. 2(a) is diagram about data related to diffracted rays and fluorescent X-rays at a first position and FIG. 2(b) is a diagram related to data of diffracted X-rays and fluorescent X-rays at a second position.

Thus, when measurements at two types of position are completed, data including diffracted X-rays and fluorescent X-rays as shown in FIGS. 2(a), (b) is obtained.

Figure 3:
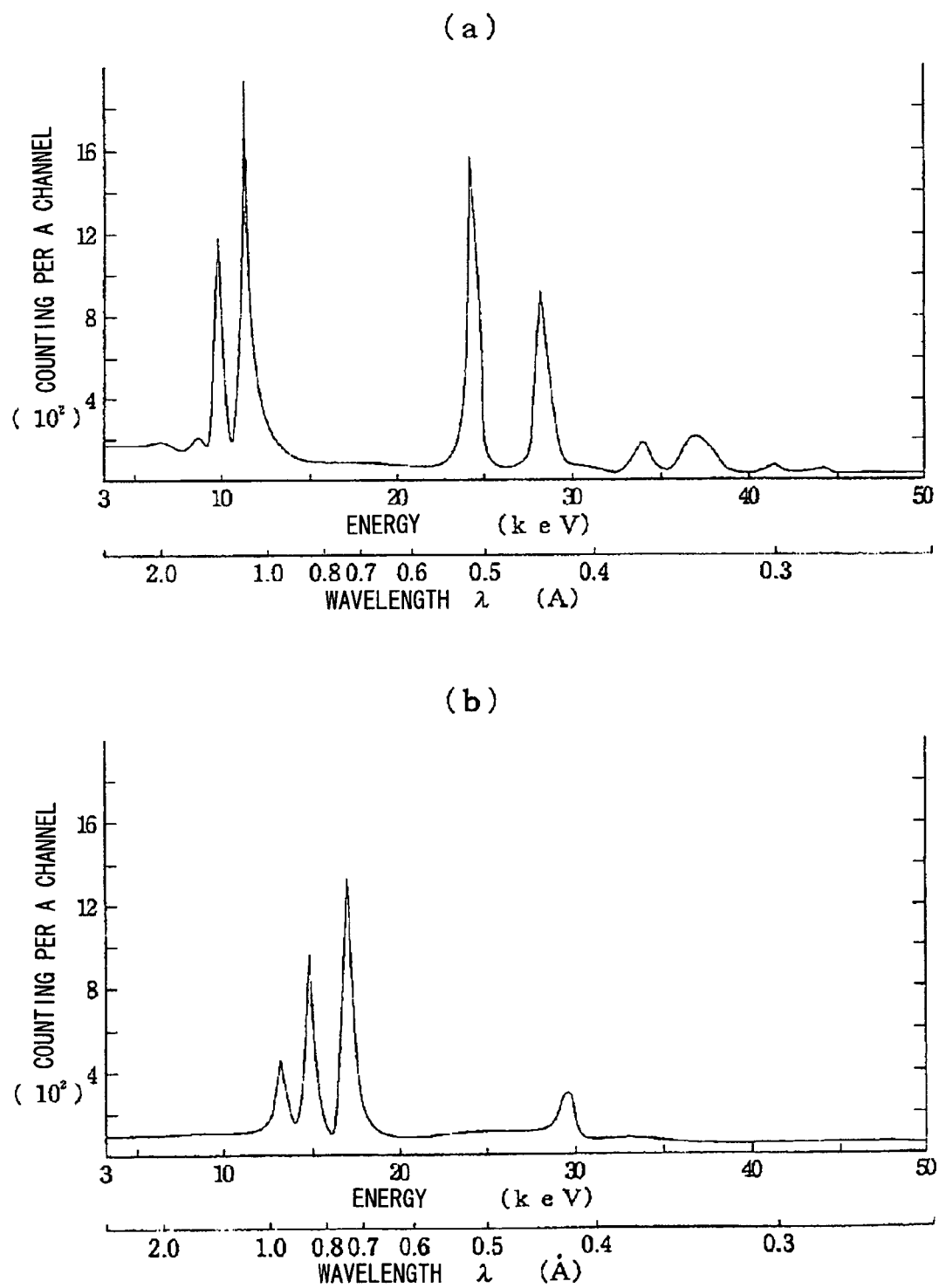
FIG. 3(a) is a diagram related to data of only diffracted X-rays and FIG. 3(b) is a diagram related to data of only fluorescent X-rays.

On the other hand, fluorescent X-rays emerge at the same position, and therefore when data of these two measured graphics are cancelled out with each other, only peaks of fluorescent X-rays are erased and diffracted X-rays with positive and negative signs remain. Of the data with these signs, if, for example, only the data with positive signs are collected and the data with negative signs are discarded, data with only diffracted X-rays obtained at the first position as shown in FIG. 3(a) are obtained. Furthermore, if the data with positive signs are discarded and only the data with negative signs are collected, only data with diffracted X-rays at the second position are obtained.

That is, since the first measured graphic and second measured graphic include data of the same fluorescent X-rays, if these are cancelled out, it is possible to obtain third data with only diffracted X-rays.

Next, by cancelling out the corresponding third data from any one of the first and second measured graphic data, it is possible to extract data with only fluorescent X-rays as shown in FIG. 3(b).

As described above, it is preferable to perform the following processing when obtaining data with only diffracted X-rays and data with only fluorescent X-rays.

That is, it is preferable to measure X-ray intensity for each level of energy at two positions having different angles, and then cancelling out data at the same energy level as described above. The data is then sorted between diffracted X-rays and fluorescent X-rays.

More specifically, assuming that m is a positive number (normally 1 to 3) and $\sigma$ (standard deviation)$=\sqrt{N}$ (N is a measured value at a certain energy level), if $m\sigma$ is used as a threshold and data with only diffracted X-rays are obtained, only the data with an energy level at which the difference between data with the same energy level equals or exceeds $m\sigma$ are kept and the rest of the data are set to 0. On the other hand, when data with only fluorescent X-rays are obtained, only the data with an energy level at which the difference between data with the same energy level falls below $m\sigma$ are kept and the rest of the data are set to 0.

In this way, it is possible to obtain data with only diffracted X-rays and data with only fluorescent X-rays with errors and with high accuracy.

INDUSTRIAL APPLICABILITY

The present invention can downsize the device for analyzing various types of specimen, and is thereby applicable as a handy-type specimen analyzer or the like.

DESCRIPTION OF SYMBOLS 1 specimen support
2 white X-ray generating means
3 X-ray detecting means
S specimen

The invention claimed is:
1. An energy dispersion type X-ray diffraction/spectral device comprising:
   a white X-ray generating means;
   an X-ray detecting means; and
   a specimen support interposed between said white X-ray generating means and said X-ray detecting means, said specimen support having positioning members which are capable of positioning said white X-ray generating means and said X-ray detecting means relative to each other in either a first position or a second position without the use of a goniometer;
   wherein said X-ray diffraction/spectral device obtains intensity data for each level of energy at the first position to obtain first data and at the second position to obtain second data;
   wherein said X-ray diffraction/spectral device obtains third data which is data regarding diffracted X-rays and is based on a difference between said first data and said second data; and
   wherein said X-ray diffraction/spectral device obtains data regarding fluorescent X-rays from the difference between the first or second data and third data.

2. An energy dispersion type X-ray diffraction/spectral device comprising:
- a white X-ray generating means;
- an X-ray detecting means; and
- a specimen support interposed between said white X-ray generating means and said X-ray detecting means, said specimen support having positioning members which are capable of positioning said white X-ray generating means and said X-ray detecting means relative to each other in either a first position or a second position without the use of a specimen rotation mechanism;
- wherein said X-ray diffraction/spectral device obtains intensity data for each level of energy at the first position to obtain first data and at the second position to obtain second data;
- wherein said X-ray diffraction/spectral device obtains third data which is data regarding diffracted X-rays and is based on a difference between said first data and said second data; and
- wherein said X-ray diffraction/spectral device obtains data regarding fluorescent X-rays from the difference between the first or second data and third data.

3. An energy dispersion type X-ray diffraction/spectral device comprising:
- a white X-ray generating means;
- an X-ray detecting means;
- a data processing means; and
- a specimen support interposed between said white X-ray generating means and said X-ray detecting means, said specimen support having positioning members which are capable of positioning said white X-ray generating means and said X-ray detecting means relative to each other in either a first position or a second position;
- wherein said X-ray detecting means obtains intensity data for each level of energy at the first position to obtain first data and at the second position to obtain second data; and
- said data processing means obtains third data which is data regarding diffracted X-rays and is based on a difference between said first data and second data, and said data processing means obtains data regarding fluorescent X-rays from the difference between the first or second data and third data.

* * * * *